United States Patent [19]

Moonen et al.

[11] Patent Number: 5,685,305
[45] Date of Patent: Nov. 11, 1997

[54] METHOD AND SYSTEM FOR MRI DETECTION OF ABNORMAL BLOOD FLOW

[75] Inventors: Chrit T. W. Moonen; Jeff Duyn; Peter van Gelderen, all of Kensington, Md.

[73] Assignee: The United States of America as represented by the Department of Health and Human Services, Washington, D.C.

[21] Appl. No.: 286,783

[22] Filed: Aug. 5, 1994

[51] Int. Cl.$^6$ .................................................. A61B 5/055
[52] U.S. Cl. ............................ 128/653.3; 128/653.4; 128/654; 324/306
[58] Field of Search ........................ 128/653.2, 653.3, 128/653.4, 654, 660.01, 662.01, 661.08, 662.02; 324/306, 309

[56] References Cited

U.S. PATENT DOCUMENTS

| | | |
|---|---|---|
| 4,021,726 | 5/1977 | Garroway et al. . |
| 4,070,611 | 1/1978 | Ernst . |
| 4,692,767 | 9/1987 | Bielke . |
| 4,855,679 | 8/1989 | Granot . |
| 4,983,917 | 1/1991 | Le Roux . |
| 4,984,573 | 1/1991 | Leunbach . |
| 4,993,414 | 2/1991 | Macovski et al. . |
| 5,010,300 | 4/1991 | Paley et al. . |
| 5,043,665 | 8/1991 | Kuhara et al. . |
| 5,079,505 | 1/1992 | Deimling et al. . |
| 5,089,784 | 2/1992 | Yoshitome et al. . |
| 5,126,673 | 6/1992 | Hennig . |
| 5,162,730 | 11/1992 | Schmitt et al. . |
| 5,190,744 | 3/1993 | Rocklage et al. ............ 128/653.4 |
| 5,195,524 | 3/1993 | Takiguchi et al. . |
| 5,203,332 | 4/1993 | Leunbach . |
| 5,212,448 | 5/1993 | Le Roux et al. .............. 324/309 |
| 5,227,725 | 7/1993 | Cory et al. . |
| 5,243,283 | 9/1993 | Tokunaga et al. . |
| 5,260,656 | 11/1993 | Cory . |
| 5,270,654 | 12/1993 | Feinberg et al. . |
| 5,281,916 | 1/1994 | Hinks et al. . |
| 5,291,891 | 3/1994 | Foo et al. . |
| 5,298,862 | 3/1994 | Hennig . |
| 5,300,886 | 4/1994 | Moonen . |
| 5,303,705 | 4/1994 | Nenov . |
| 5,322,682 | 6/1994 | Bartzokis et al. ............ 128/653.4 |
| 5,327,085 | 7/1994 | Cory . |
| 5,327,087 | 7/1994 | Hafner et al. . |
| 5,327,088 | 7/1994 | Pipe . |
| 5,335,660 | 8/1994 | Dumoulin ..................... 128/653.4 |
| 5,352,979 | 10/1994 | Conturo ........................ 128/653.4 |
| 5,377,681 | 1/1995 | Drane ........................... 128/653.4 |

FOREIGN PATENT DOCUMENTS

WOA 91
14186    9/1991    WIPO .

OTHER PUBLICATIONS

Magnetic Resonance In Medicine, vol. 29, 1993, pp. 485–497, N. Wilke et al. "Contrast–Enhanced First Pass Myocardial Perfusion Imaging: Correlation Between Myocardial Blood Flow in Dogs at Rest and During Hyperemia".

Journal of Magentic Resonance, vol. B101, 1993, pp. 106–109, I. J. Lowe, R. E. Wysong, "Dante Ultrafast Imaging Sequence (DUFIS)".

Radiology, vol. 176, 1990, pp. 211–220, R. R. Edelman et al., "Cerebral Blood Flow: Assessment with Dynamic Contrast–enhanced T2*–weighted MR Imaging at 1.5 T".

Radiology, vol. 185, 1992, pp. 795–801, S. Schaefer et al., "Evaluation of Myocardial Perfusion Abnormalities with Gadolinium–enhanced Snapshot Imaging in Humans".

*Primary Examiner*—Brian L. Casler
*Attorney, Agent, or Firm*—Morgan & Finnegan L.L.P.

[57] ABSTRACT

A magnetic resonance imaging system and method for detecting blood flow abnormalities according to the time delay for the arrival of a bolus of a MR contrast agent into localized regions as observed in a temporal series magnetic resonance signals or images obtained subsequent to bolus injection. A rapid series of imaging pulse sequences acquires the time development of the signal from localized regions within the imaged field of view of a body. During the imaging period, a bolus of a MR contrast agent is injected into the cardiovascular system of the body. As the MR contrast material circulates through the imaged region, the associated field gradient which extends into the surrounding tissue results in signal losses in the acquired signal from these regions. The arrival time for the bolus into a given localized region is determined from the acquired time data, and the relative arrival time among regions in the imaged field of view indicates whether there is decreased blood flow to certain areas.

16 Claims, 9 Drawing Sheets

METHOD AND SYSTEM FOR MRI DETECTION OF ABNORMAL BLOOD FLOW

TECHNICAL FIELD

The present invention relates generally to magnetic resonance imaging, and more particularly to an in vivo magnetic resonance imaging method and system for detecting blood flow variations and abnormalities.

BACKGROUND OF THE INVENTION

Blood flow variations and abnormalities are often associated with serious and often life-threatening conditions. Rapid identification and localization of such abnormalities is highly desirable in order that the appropriate corrective action, be it therapeutic or surgical, may be taken promptly. For instance, the measurement of cerebral perfusion is an important element in the study of both normal and impaired human brain function. The connection between brain activity and perfusion has been well established. Altered perfusion has been observed in several diseases, including brain infarction, tumors, and neurodegenerative disorders. In the case of cerebral ischemia any delay in post-ischemic recirculation and reoxygenation of brain tissue reduces neuronal survivability. Similarly, arterial stenosis is associated with stroke or cardial infarction which may be averted by early detection and treatment.

Arterial stenosis is usually diagnosed using direct monitoring of contrast agent passage. A catheter is placed close to the suspected stenosis, contrast agent is injected, and rapid images are detected by X-ray, CT, fluoroscope, digital angiography. Similarly, in the brain, perfusion has been measured using techniques such as Doppler Ultrasound Imaging, PET, Xenon-CT, and SPECT.

Magnetic resonance imaging (MRI) has also been used successfully to study blood flow in vivo. Among the techniques that have been employed, many are the subject matter of prior U.S. patents (e.g., U.S. Pat. Nos. 4,983,917, 4,993,414, 5,195,524, 5,243,283, 5,281,916, and 5,227,725), and are generally related to measuring blood flow with or without the use of a bolus, some of these techniques referred to in the art as MRI angiography. Many such techniques are directed to measuring the signal from moving moieties (e.g., the signal from arterial blood water) in the vascular compartment, not from stationary tissue. Thus, images are based directly on water flowing in the arteries, for example.

In the brain, several researchers have studied perfusion by dynamic MR imaging using an intravenous bolus administration of a contrast agent in both humans and animal models (See, A. Villringer et al, *Magn. Reson, Med.*, Vol. 6 (1988), pp 164–174; B. R. Rosen et al, *Magn. Reson. Med.*, Vol. 14 (1999), pp. 249–265; J. W. Belliveau et al, *Science*, Vol. 254 (1990), page 716). These methods are based on the susceptibility induced signal losses upon the passage of the contrast agent through the microvasculature. Although these methods do not measure perfusion (or cerebral blood flow, CBF) in classical units, they allow for evaluation of the related variable rCBV (relative cerebral blood volume). In U.S. Pat. No. 5,190,744 to Rocklage, quantitative detection of blood flow abnormalities is based on the rate, degree, duration, and magnitude of signal intensity loss which takes place for the region of interest following MR contrast agent administration as measured in a rapid sequence of magnetic resonance images. It may be appreciated that blood volume measurements in the brain based on tracking the passage of a bolus of contrast agent require a time-resolution of the order of 1 s per image due to the short transit time of blood. The requirement of rapid imaging is generally associated with a sacrifice of signal-to-noise which limits detection based on manipulation of actual quantitative values. Also, spurious effects due to, for example, colateral blood supply, may limit the amount of signal change measured from a local region that has an actual blood deficit.

Therefore, although these techniques have demonstrated their utility, there remains a need for further improvements in MRI detection of blood flow variations and abnormalities.

SUMMARY OF THE INVENTION

It is, therefore, an object of the present invention to provide an improved method for detecting blood flow variations and abnormalities.

A related object of the present invention is to provide an MRI method for detecting blood perfusion variations and abnormalities in the brain or in any vascular compartment.

Another object of the present invention is to provide an MRI method for detecting blood perfusion variations and abnormalities based on signals acquired from stationary tissue.

A further object of the present invention is to provide an MRI method for detecting blood perfusion variations and abnormalities based on the arrival time of a bolus of MR contrast agent as determined from the signals acquired from stationary tissue.

The present invention achieves these and other objects, and overcomes limitations of the prior art, by providing a method and system for detecting blood flow abnormalities according to the time delay for the arrival of a bolus of a MR contrast agent into localized regions as observed in a temporal series magnetic resonance signals or images obtained subsequent to bolus injection. The present invention provides a method and system of generating magnetic resonance imaging information for detecting regions of abnormal blood flow in a body, which includes the steps of: (a) injecting a bolus of a magnetic resonance imaging contrast agent into the cardiovascular system of the body; (b) subjecting the body to a magnetic resonance imaging pulse sequence for obtaining a series of temporally spaced magnetic resonance signals or images from localized regions in at least a part of said body into which the contrast agent passes; (c) and providing an arrival delay time from the signals or images for the localized regions. Further, the method provides arrival delay time maps for visual observation of detected regions of abnormal blood flow.

BRIEF DESCRIPTION OF THE DRAWINGS

Additional aspects, features, and advantages of the invention will be understood and will become more readily apparent when the invention is considered in the light of the following description made in conjunction with the accompanying drawings, wherein.

DETAILED DESCRIPTION OF THE PREFERRED EMBODIMENT

Figure 1:
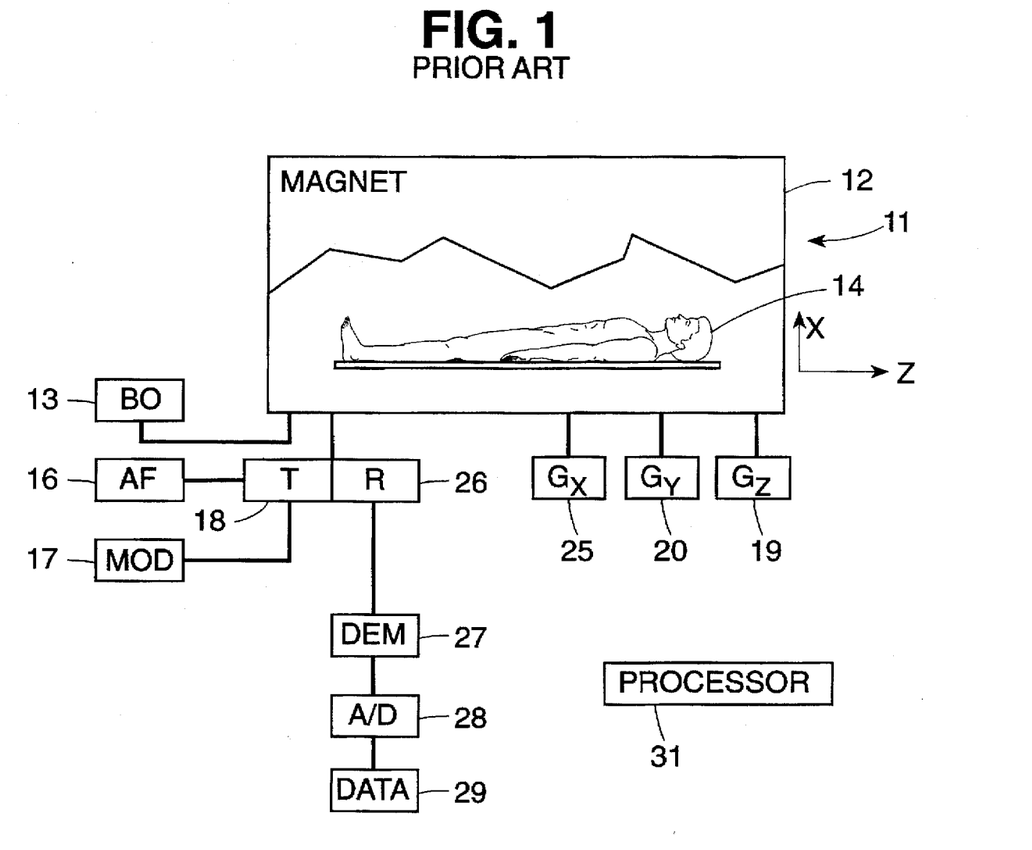
FIG. 1 is a block diagram of a magnetic resonance (MR) system used in accordance with the present invention.

Before consideration in detail of the present invention, a brief overview of a conventional MRI system is in order. In particular, FIG. 1 shows in block diagram form an in vivo NMR imaging system which is capable of receiving a patient 14. The system includes a magnet 12 for generating a large static magnetic field. The magnet is sufficiently large to have a bore into which a patient 14 can fit. The patient 14 is positioned and the magnetic field is generated by a magnetic field generator indicated at 13 by block $B_o$. RF pulses are generated utilizing RF generator 16, and the RF pulses are shaped using modulator 17. The shape of a modulated pulse could be any predetermined shape, and for example may be Gaussian or Sinc (i.e., sin(bt)/bt, where b is a constant, and t is time). Shaped pulses are usually employed in order to shape and limit the bandwidth of the pulse, thereby restricting excitation by the RF pulse to spins that have Larmor frequencies within the RF pulse bandwidth. A RF pulse signal is transmitted to coils in the magnet assembly which are not shown. The coils may be surface coils, body coils, limb coils or head coils, for example. The duration and amplitude of the RF pulse determine the amount which the net magnetization is "tipped".

Gradient generators 25, 20, and 19, which include respective gradient coils, produce the $G_x$, $G_y$, and $G_z$ magnetic fields in the direction of the polarizing magnetic field $B_o$, but with gradients directed in the x, y, and z directions, respectively. The use of the $G_x$, $G_y$, and $G_z$ magnetic field gradients is well known in the art, including such uses as dephasing or rephasing excited spins, spatial phase encoding or spatial gradient encoding acquired signals, and spatial encoding of the Larmor frequency of nuclei for slice selection.

Induced nuclear magnetic resonance signals are detected by receiver coils in the magnet which are not shown. The receiver coils and the transmitter coils may be the same, with a transmit/receive (T/R) switch being used to select transmission or reception of radio frequency signals to or from the coils, respectively. The received signal is demodulated by demodulator 27, and the demodulated signal is amplified and processed in the analog-to-digital processing unit 28 to provide data as indicated at 29. The entire process is monitored and controlled by the processor means 31 which, according to the functional block diagram of FIG. 1 and to components found in known commercial or experimental systems that are used to control and monitor the entire process, includes components necessary to control the timing, amplitudes and shapes of the control signals for the various elements of the MRI system and typically includes programming, computing, and interfacing means.

In accordance with the present invention, such a conventional magnetic resonance imaging system is controlled according to a rapid series of imaging pulse sequences that acquires the time development of the signal from localized regions within the imaged field of view of a body placed in the imaging region. During the imaging period, a bolus of a MR contrast agent is injected into the cardiovascular system of the body. As the MR contrast material circulates through the imaged region, the associated field gradient which extends into the surrounding tissue results in signal losses in the acquired signal from these regions. The arrival time for the bolus into a given localized region may be determined from the acquired time data, and the relative arrival time among regions in the imaged field of view indicates whether there is decreased blood flow to certain areas. Each of these steps, and preferred modes for practicing them, is further described in the ensuing description.

As mentioned, tracking a bolus of MR contrast agent as it passes through the cardiovascular system, and into the field of view that is being imaged requires a fast imaging sequence which provides a time resolution sufficient to sample the time varying signal. It is understood that in accordance with the present invention, the acquired signals originate from stationary tissue. The information about blood flow is indirectly encoded in the signal amplitude of stationary water in an area nourished by the particular artery. Changes in signal amplitude are brought about by the passage of MR contrast material leading to field distortions in the regions of the stationary water.

A preferred MR imaging technique is the subject of U.S. application Ser. No. 08/205,434 (invented by one of the inventors of the present invention), filed on Mar. 4, 1994, and which is hereby incorporated by reference. This technique, called Frequency Shifted (FS)-BURST, allows for scanning of the whole brain within a few seconds. For bolus tracking, the attractive feature of this method is the fact that it has, unlike EPI (echo planar imaging) and segmented FLASH (Fast Low Angle SHot), equal T2-weighting over all k-space lines.

Conventional BURST imaging is a class of ultra fast imaging techniques initially proposed by Henning et at. ("Fast Imaging Using BURST Excitation Pulses" in "Proceedings, 7th Annual Meeting, Society of Magnetic Resonance in Medicine, 1988", p. 238), and successfully implemented in a two-dimensional (2D) version by Lowe et al. ("DANTE Ultrafast Imaging Sequence (DUFIS)", J. Magn. Reson. B. 101, pp. 106–109 (1993)) on a small-bore animal scanner. A version with improved signal to noise ratio (SNR) has been proposed by Le Roux et al ("BURST Ultrafast Excitation Pulses" in "Proceedings, 7th Annual Meeting, Society of Magnetic Resonance in Medicine, 1991", p. 269).

Conventional BURST excites a set of equally spaced, narrow strips in an object, and creams an image from a single slice, perpendicular to the direction of the strips. In order to average, to scan multiple slices, or to perform three-dimensional (3D) imaging, repeated excitation of the same strips is required. The FS-BURST technique is directed to a method which overcomes the problems associated with prior art BURST methods and allows for 3D volumes to be scanned within a few seconds.

According to FS-BURST technique, a set of equally spaced narrow strips of an object are excited utilizing a BURST type RF pulse. The BURST type RF pulse includes a plurality of evenly spaced RF pulses which can include, for example, 15 to 75, and more preferably about 25 to 50 pulses of equal strength. From the excited strips, an image from a single slice, perpendicular to the direction of the strips is obtained. In order to obtain a 3D image a series of imaged slices is collected. However, in order to avoid repeated excitation of the same strips and resulting saturation, according to the FS-BURST method, on successive repetitions the location of the excited strips are shifted. This shifting is performed by adding incremental offsets to the RF-frequency of the BURST type RF pulse.

Figure 2:
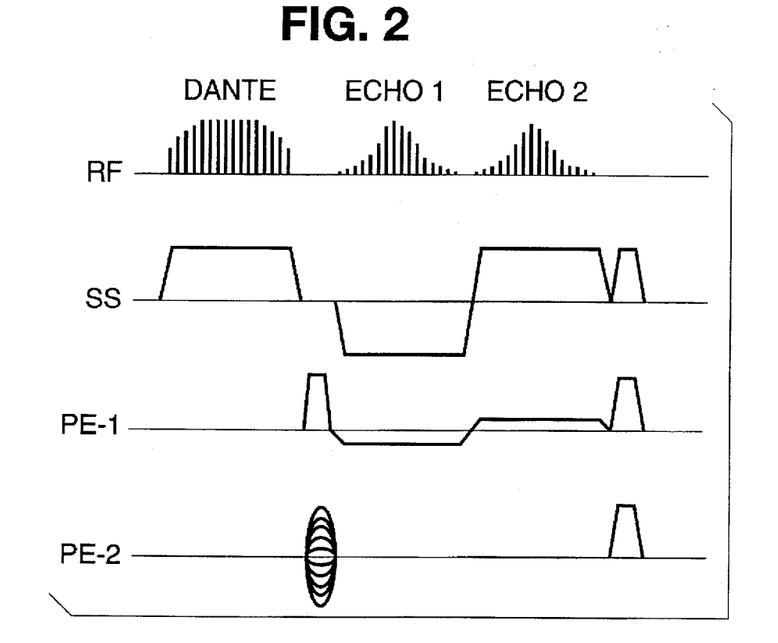
FIG. 2 illustrates a 3D FS-BURST pulse sequence as employed in accordance with an embodiment of the present invention.

FIG. 2 illustrates a three dimensional (3D) FS-BURST pulse sequence. The excitation consists of a Hamming-apodized BURST RF-pulse in combination with a slice selection (SS) gradient. Two echo trains (ECHO 1, ECHO 2) are created by repeated gradient reversal. Both echo trains are phase encoded in two directions by PE-1 and PE-2. A gradient crusher is shown applied after collection of the second echo. As discussed, successive BURST RF-pulses are frequency shifted.

Figure 3A:
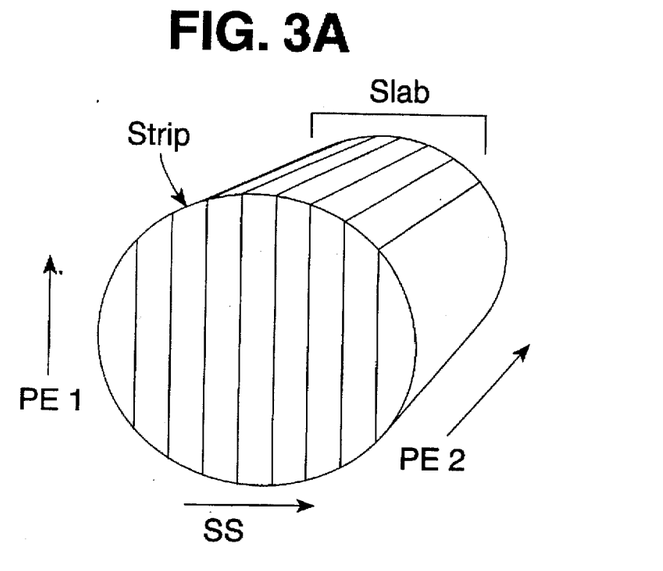
FIG. 3A schematically illustrates strip selection according to a 3D FS-BURST pulse sequence.
Figure 3B:
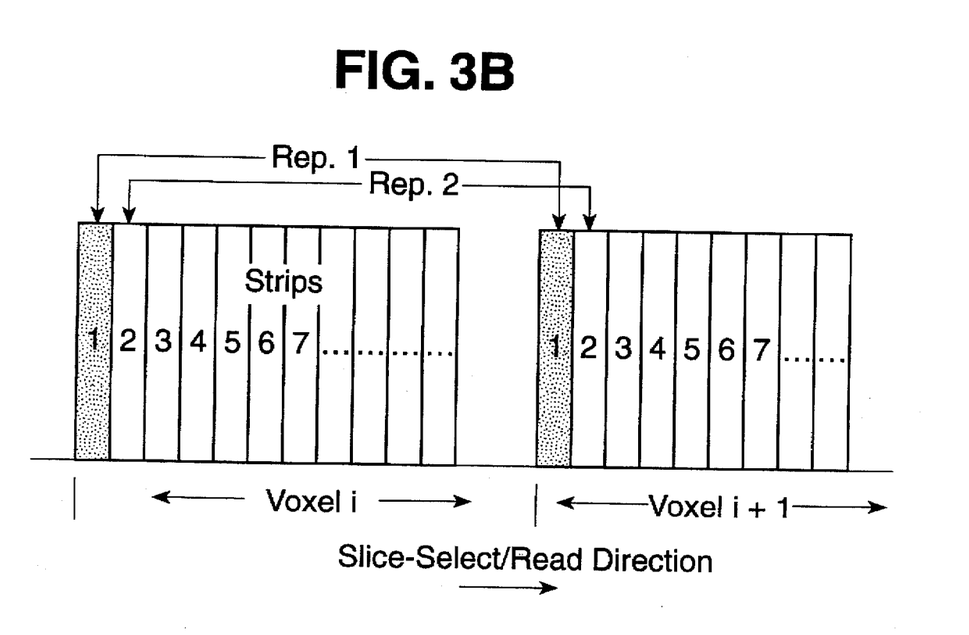
FIG. 3B schematically illustrates shifting of the strip location for adjacent voxels on successive repetitions of a 3D FS-BURST pulse sequence.

FIGS. 3A and 3B illustrate strip selection and shifting within a slab in a cylindrical object according to a 3D FS-BURST pulse sequence. The strip shaped regions, excited with the BURST RF pulse, run parallel to phase encoding gradients PE-1 and PE-2, and perpendicular to the slice select (SS) gradient. As shown in FIG. 3B, for each repetition time TR, a single strip is excited within each imaging voxel. On successive repetitions (e.g., rep. 1 and rep. 2 in FIG. 3B), the RF transmitter frequency is shifted resulting in a shift of the strip locations. FIG. 3B illustrates a single strip shift protocol, although it may be understood that multiple strip shift protocols may be employed.

As mentioned, in practice, 3D datasets on a human brain can be collected within a few seconds utilizing a standard clinical scanner at 1.5 Tesla. An advantage of the FS-BURST technique over other fast imaging techniques is that it is less demanding with regard to gradient slew rates, even at very high imaging speeds. The small number of gradient switchings in the BURST type RF excitation pulses lessens demand on gradient slew rates, and reduces eddy current effects.

In the FS-BURST imaging technique all echoes of the second echo train have identical $T_2^*$ weighing. This makes FS-BURST a preferable imaging pulse sequence for suspectibility-based neuro-imaging experiments, and particularly 3D bolus tracking imaging as employed in the present invention for detecting abnormal blood flow based on the arrival time delay of the bolus of MR contrast agent.

It is understood, however, that although FS-BURST is a preferred image acquisition sequence, many other image acquisition techniques may be used in accordance with the present invention including, for example, echo-planar imaging (EPI), FLASH, and echo-shifted FLASH (ES-FLASH), each with its own advantages and disadvantages.

As may be appreciated, images are preferably acquired continuously before, during and after contrast injection so that the entire time course of the contrast agent passage through the imaged region may be acquired. Further, image acquisition prior to bolus injection assists assessment of an initial baseline signal. The literature is replete with possible contrast agents, and several examples of preferred contrast agents include those containing paramagnetic lanthanide ions, especially high spin lanthanides such as ions of Dy, Gd, Eu and Ho, in particular Dy(III). Also, many suitable paramagnetic metal chelate MR contrast agents are known in the art, and may be used as preferred contrast agents. Administration of such contrast agents, including the appropriate dosage, is well known to one skilled in the art, and the location of administration into the cardiovascular system is generally related to the region of the body that is being imaged. For example, when imaging blood flow in regions of the brain, injection of a bolus of contrast agent may occur in the antecubital vein.

Preferably after the time series of images all have been acquired, data manipulation is performed to elucidate regions within the imaged field of view that are associated with blood flow abnormalities or variations. In accordance to the present invention, the arrival time of the contrast agent is a parameter which is used for detecting regions of abnormal blood flow. The arrival time depends on bulk flow, flow velocity in the major arteries, and perfusion in tissue, and thus carries the information about blood flow abnormalities and variations, and more particularly, about stenosis, blood flow deficits, and associated pathologies (e.g., ischemia).

Figure 4:
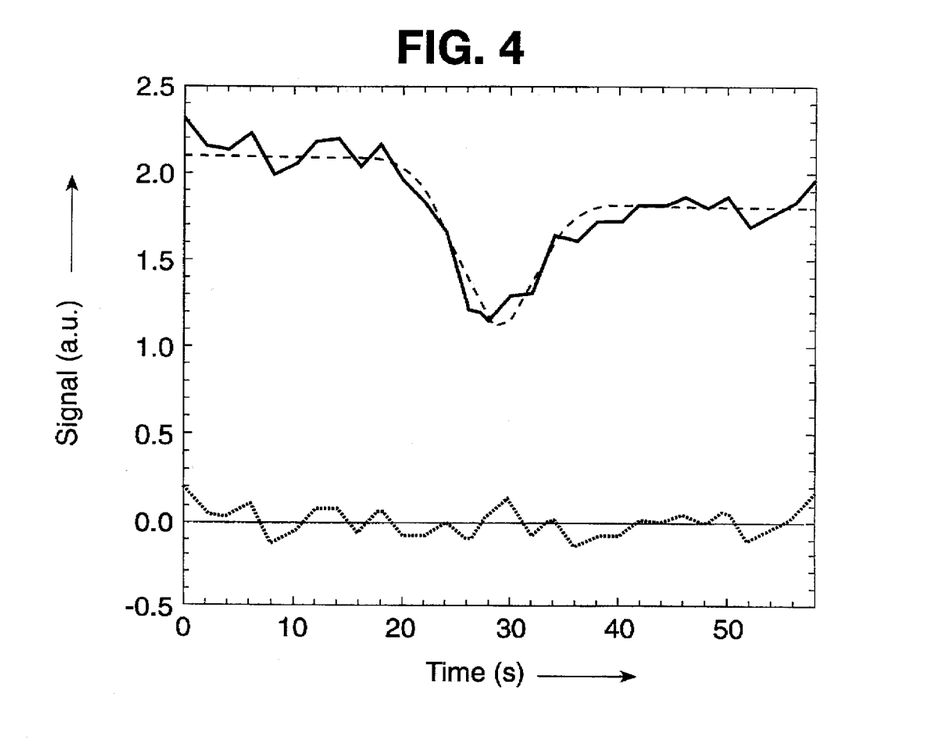
FIG. 4 shows a typical time course data, signal intensity as a function of time (solid line connecting signal intensity points), together with a fitted time-curve (dashed line) and fit residuals (dotted line) from a grey-matter pixel of normal brain, in accordance with the present invention.

FIG. 4 generally illustrates the time development of the signal intensity for a particular voxel (or pixel). The solid line connects actual signal intensity points that are separated by the time interval between successive image acquisitions, which in this example, which is further discussed hereinbelow, is about 2.13 seconds. As may be appreciated, there are many ways to assess the arrival time based on such a signal. A preferred method is to fit an analytical curve, shown by the dashed curve, to the acquired signal using numerical methods, and then use a definable point associated with the fit to represent the arrival time. For instance, the arrival time may be defined as the time that the maximum signal loss occurs within the time interval during which the contrast agent traverses the region within the voxel. By performing this analysis for each voxel (or pixel) within the field of view or an area of interest, as described above, the arrival time of the bolus in a pixel is indicative of blood flow abnormalities or variations.

As may be readily understood, the absolute value of the arrival time for any given voxel (pixel) is an arbitrary value that depends on what is defined as the starting time. For convenience, the time of bolus injection or the time of the first imaging sequence acquisition may be defined as the starting time. That is, it may be understood that since detecting blood flow abnormalities and variations according to the present invention preferably compares the arrival time for a plurality of pixels, the absolute value of the starting reference time is not critical, provided the same starting reference time is used for the all voxels (pixels) that are analyzed.

Preferably, a method of identifying regions of decreased blood flow involves generating an "arrival time map" (also referred to as "arrival delay time map" and "arrival delay map"). An arrival time map is a two-dimensional image in which each pixel (corresponding to a localized region) of the image is assigned an intensity or color value (or other visual characteristic) according to its associated arrival delay time. For example, for each pixel a gray scale level may be assigned based on the arrival delay time value. Regions of abnormal blood flow, therefore, may be visually identified in the arrival delay map.

The following example is presented to illustrate features and characteristics of the present invention, which is not to be construed as being limited thereto.

EXAMPLE

In this example, a 3D bolus tracking MR technique for perfusion imaging of human brain was practiced in accordance with the present invention for detecting abnormalities and variations in blood flow based on the delay in arrival of a bolus of MR contrast agent. All experiments were performed on standard 1.5 T GE/SIGNA clinical scanners. Five normal volunteers, and one patient with a sub-acute brain infarct were studied. Modified (Frequency-Shifted: FS) BURST MRI was performed during injection of a bolus of Gd-DTPA (0.13 mmol per kg subject weight) in the antecubital vein. 3D datasets were acquired with a time resolution of 2.2 s and an effective spatial resolution of 4.3×4.3×6.4 mm. 3D maps of blood volume and bolus arrival time were determined by fitting a synthetic curve to the intensity time course on a voxel by voxel basis.

All experiments were performed on standard 1.5 T GE/SIGNA clinical scanners (GE Medical Systems, Milwaukee), equipped with 10 mT/m, actively shielded whole body gradients. A standard quadrature head RF coil was used. Five normal volunteers, and one patient with a sub-acute brain infarct were studied. The subject with acute infarction was diagnosed with a left middle cerebral artery occlusion and was scanned 3 days post-ictus.

The MR method used for 3D bolus-tracking was based on FS-BURST, which described above. The essentials of this method can be summarized as follows. Excitation of magnetization is performed by a BURST-pulse, which consists of a train of evenly spaced, low flip-angle rf-pulses in combination with a slice select gradient. Multiple trains of measurable echo signals can be generated by repeated reversal of the selection gradient (FIG. 1). By applying a second switched gradient (PE1 in FIG. 1), a second dimension of spatial encoding is incorporated in each echo train, allowing scanning of a complete image plane within a single repetition of the sequence. The addition of a third gradient (PE2), of which the amplitude is varied over subsequent repetitions of the sequence, allows scanning of 3D volumes. Saturation effects were avoided by applying a frequency shift to the RF pulse on successive repetitions (i.e., FS-BURST).

For 3D bolus tracking, the original sequence was modified on the following points:

1. Instead of acquiring two echo trains, for 3D bolus tracking only the second echo train was collected. It has been shown that the second echo train has an inherent uniform T2*-weighting, this in contrast with the first echo train. This allows for susceptibility-weighted scanning without image artifacts.
2. For practical convenience, a reduction of the scan time was established by reducing the number of sample points and the size of the field of view.
3. The effective echo time of the second echo train was reduced to improve contrast-to-noise ratio.

Furthermore, a single-strip shift protocol was chosen.

The BURST RF pulse consisted of a train of 48 evenly spaced pulses. The pulse spacing was 288 μs, the total BURST pulse length 13.7 ms. The individual RF pulses were 128 μs long, and were apodized with a combination of a sine and a gaussian function. In combination with selection gradients, applied simultaneously in antero-posterior and superoinferior directions, this resulted in selection of a 150 mm thick slab with 45° angulation. The specific angle was used to utilize the maximum effective gradient strength to achieve optimum resolution. An echo train of 40 echoes was acquired with an effective echo time of 28.8 ms. The reason for acquiring less echoes than the number of BURST RF pulses was to reduce the repetition time (TR) without affecting the selection properties of the BURST pulse. Each echo contained 36 data points. 48 phase encoded repetitions were performed using TR=45 ms. A 36×40×48 data matrix was collected using a 22 cm×16 cm×19.2 cm field o scans were recorded sequentially, resulting in a total measurement time of 65 to 87 seconds. The prolonged use of strong gradients did not result in excessive heating of the gradient coils.

For comparison, and on the normal subjects only, 2D FLASH dynamic imaging was performed with TE/TR=27/33.8 and a 128×64 data matrix. This resulted in a scan time of 2.16 seconds, equivalent to that of the 3D experiment. Between the 3D and 2D experiments, a delay of at least 30 minutes was used.

Ten seconds after the start of each dynamic imaging experiment, a bolus of Gd-DTPA solution was administered at a rate of 6 cc/sec using a mechanical injector (Medrad Inc., Pittsburgh, Pa.) through a 18 gauge catheter placed in the antecubital vein. A dose of 0.13 mmol per kg subject weight was used, resulting in injection times of 3–5 seconds (typical). For the stroke patient, a 0.15 mmol per kg dose was hand injected within 6–10 seconds.

Data processing was performed off-line using Sun-SPARC 10 workstations (Sun Microsystems, Mountainview, Calif.) using IDL processing software (Research Systems, Boulder, Colo.). Prior to 3D Fourier transformation, a 20% Hamming filter was applied over each echo, and over the second phase encode dimension. Also before Fourier transformation, the dataset was zero-filled to a 64×64×64 matrix. The effective resolution was 6.4×4.3×4.3 min. Magnitude images were then used to calculate the rCBV maps. Also calculated were maps displaying the arrival time of the bolus, i.e., "arrival time maps". The calculations were performed by least-squares fitting of a synthetic curve to the time curve of each pixel inside the brain. Several types of synthetic curves, among which a gamma-variate function were tested. The latter is a 4-parameter curve which, in cases of limited signal-to-noise ratio (SNR) and time resolution, does not result in reliable fitting. For the specific (SNR) and time resolution of our data, a 3-parameter curve of the form:

$$f(t) = (a-b)\left( e^{-((t+c)/w)^2} + 0.15\left( \frac{\pi}{2} + \arctan(1.33(t+c)/w) \right) - 0.042(t+c+1) \right)$$

with:

t=time [−1 . . . 1],
a=pre-bolus signal level (variable),
b=bolus intensity (variable),
c=bolus arrival time (variable),
w=width of bolus-passage (fixed), was used. The exponential term of the function describes a gaussian time course of signal loss during the bolus passage, whereas the arc-tangent and constant slope terms account for persistent signal loss after passage of the bolus. The function resulted in almost all (>95%) of the pixels in a convergent fit, and gave a fairly accurate representation of the signal loss during and after the passage of the bolus. The function was based on the following assumptions: a quasi-constant pre-bolus signal level (a), a quasiconstant post-bolus signal loss related to the bolus intensity proportional to bolus intensity (b), and a variable bolus arrival time (c). Monte Carlo simulations were performed to determine the propagation of measurement noise into noise in the fitted parameters. Furthermore, in order to check accuracy of the fitting procedure with respect to systematic errors, maps of the sum of squared differences between time-course data and fit-results were created, and normalized to baseline signal intensity (a).

After time-curve fitting, the rCBV maps were calculated from: rCBV=1 n (b/a). Arrival time maps were calculated from c, and thresholded with parameter b (pixels with a b value less than a fifth of the average grey matter value were set to background intensity level).

An example of a typical fit in a grey matter pixel of normal brain is shown in FIG. 4, which was generally described hereinabove. The Monte Carlo simulations resulted in estimated standard deviations for baseline signal level, rCBV, and arrival time of 1.5%, 8.0%, and 0.45 seconds, respectively.

Figure 5:
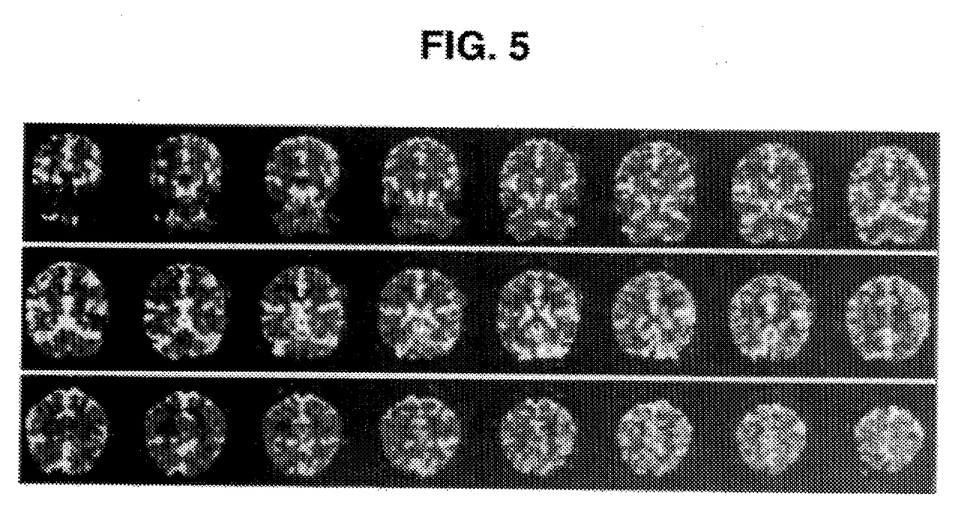
FIG. 5 shows calculated rCBV maps of 24 (out of 64) slices through the brain of a normal brain subject, in accordance with practicing the present invention.

FIG. 5 shows an example of the calculated rCBV maps from a normal subject, displayed are images from a section of 24 slices, covering about two-thirds of the brain. Subsequent slices are displayed going from the anteroinferior to postero-superior through the brain. At the bottom left, a sagittal image displays the brain slab from which the data has been obtained, as well as the angulation of the imaging slices. As expected, grey matter areas appear bright in the images, indicating a relatively high blood volume. Clearly identifiable are also the ventricular system, the sylvian fissures, and the tentorium. As observed previously by numerous other researchers, part of the ventricular system appears bright on the rCBV maps. A possible explanation is the signal loss due to macroscopic susceptibility effects during bolus-passage through the larger veins bordering the ventricles (eg. inferior sagittal sinus).

Figure 6:
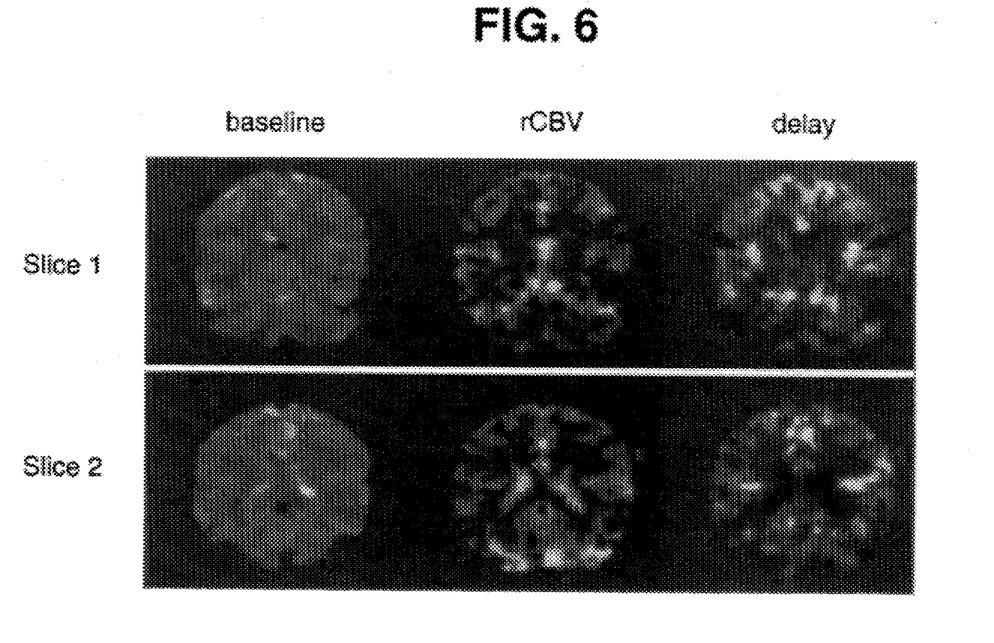
FIG. 6 illustrates the calculated baseline intensity, rCBV, and arrival time maps in two slices out of the dataset from FIG. 5.

Two slices out of this data set are shown enlarged in FIG. 6, together with corresponding baseline signal and arrival time maps. The grey scale in the arrival time maps runs from early (white) to late arrival (black) and spans 4 seconds. IN these arrival time maps, note the early bolus arrival around the larger arteries (anterior, middle and posterior cerebral arteries), especially the middle cerebral arteries in slice 1 (insular arteries indicated with black arrows). Notice the late signal shift in the ventricular system, as well as the late arrival (delay about 2-4 seconds) of the ventricular system, as well as the late arrival in the larger vessels, probably veins of the posterior brain (e.g. inferior and superior sagittal sinuses).

Figure 7A:
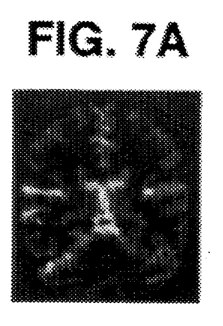
FIG. 7A and FIG. 7B illustrate calculated rCBV maps from 2D FLASH, and FS-BURST, respectively, obtained from similar sections of normal brain.
Figure 7B:
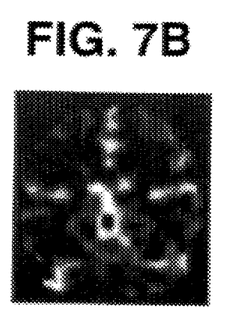
Figure 7C:
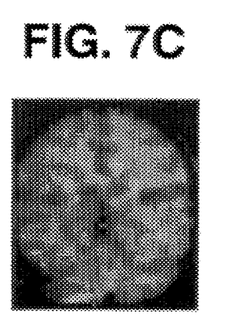
FIG. 7C displays a normalized map of the sum of squared differences between time-course data and fit results.

FIGS. 7A and 7B compare an rCBV map obtained with FLASH, and a slice out of the 3D FS-BURST rCBV dataset, respectively. This shows the general similarity for features observed by both methods. FIG. 7C shows a map of the normalized sum of squared differences between time data and fit of the FS-BURST data. The map is relatively uniform, i.e. shows only faintly recognizable structure, indicating minimal systematic fit errors. Most of the remaining structure may be attributed to differences in baseline signal intensity which may be reduced with additional data manipulation. It may be understood that the data manipulation performed in this example, including the use of the described fitting function, is merely provided as an example of determining the arrival time and generating arrival time maps. Many additional or alternative analytical and numerical techniques may be employed to provide the arrival time and to minimize error.

Figure 8A:
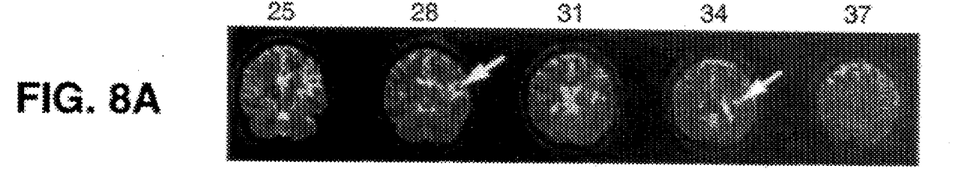
FIG. 8A shows a T2-weighted MRI of sub-acute brain infarction.
Figure 8B:
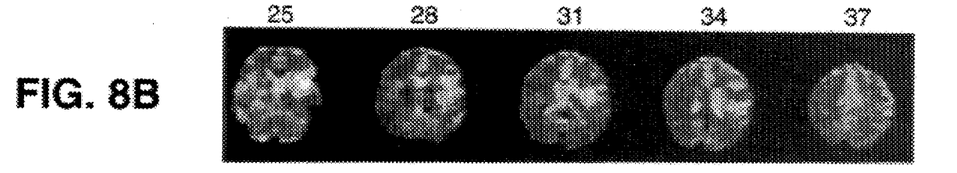
FIGS. 8B–8D show a 3D FS-BURST perfusion measurement of sub-acute brain infarction.
Figure 8C:
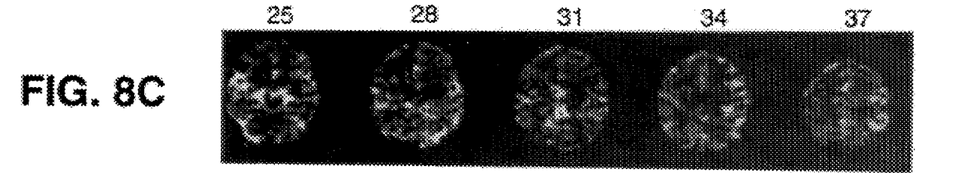
Figure 8D:
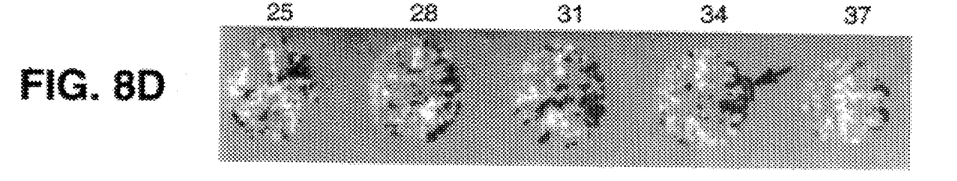
Figure 9A:
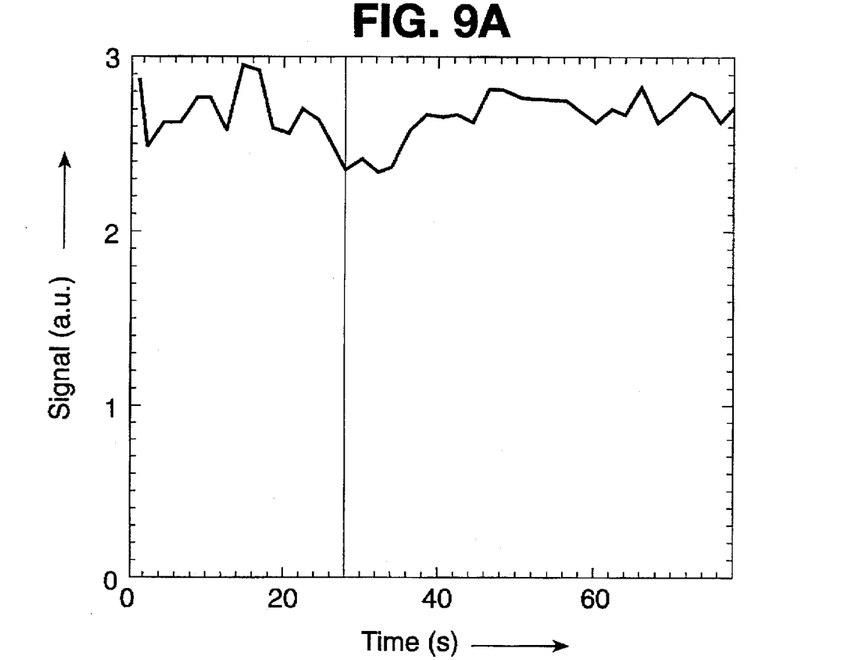
FIG. 9A shows the bolus arrival time data in sub-acute stroke from a selected pixels inside the infarct.
Figure 9B:
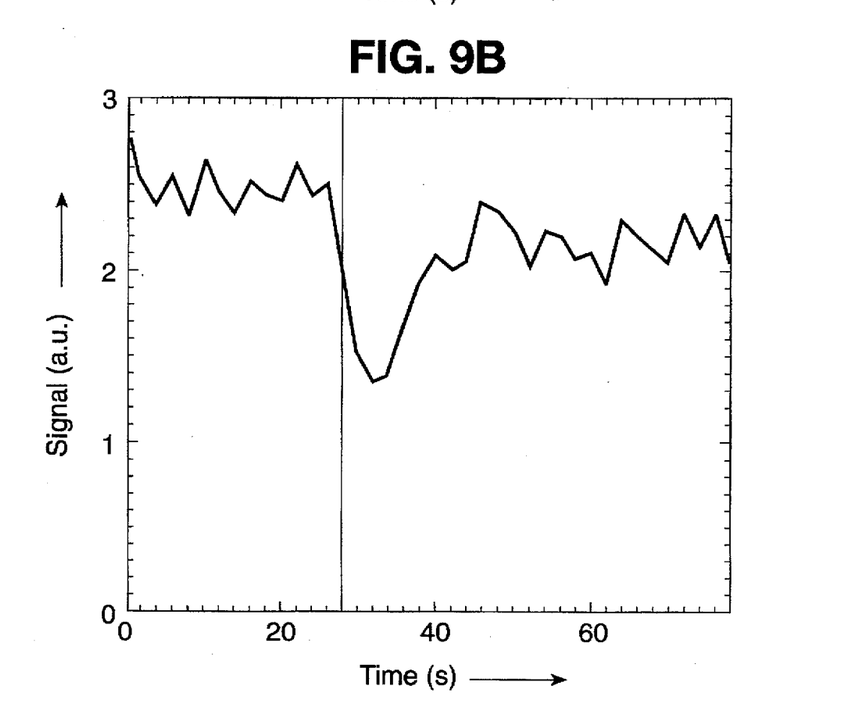
FIG. 9B and FIG. 9C show the bolus arrival time data in sub-acute stroke from respective pixels adjacent to the infarct.
Figure 9C:
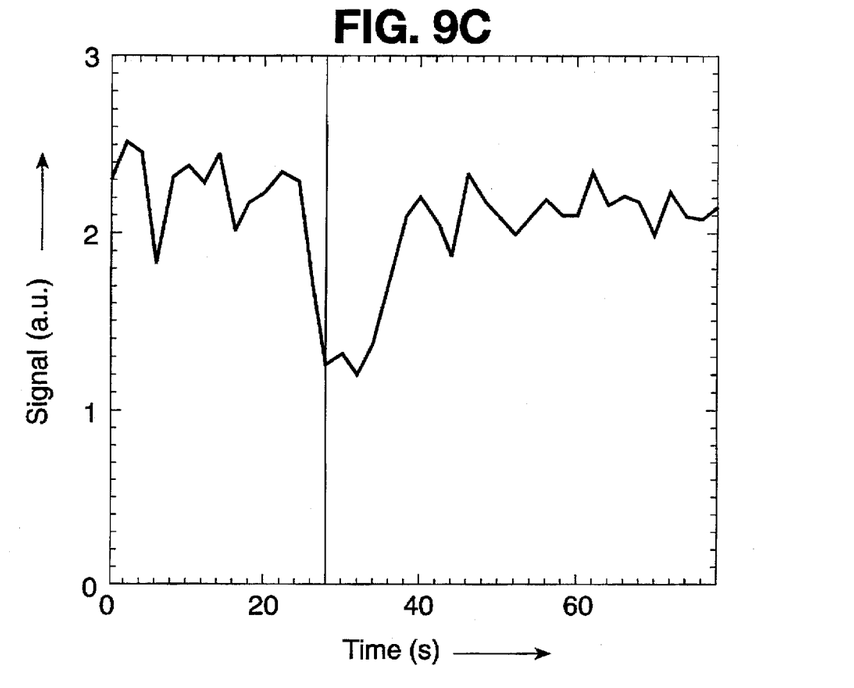
Figure 9D:
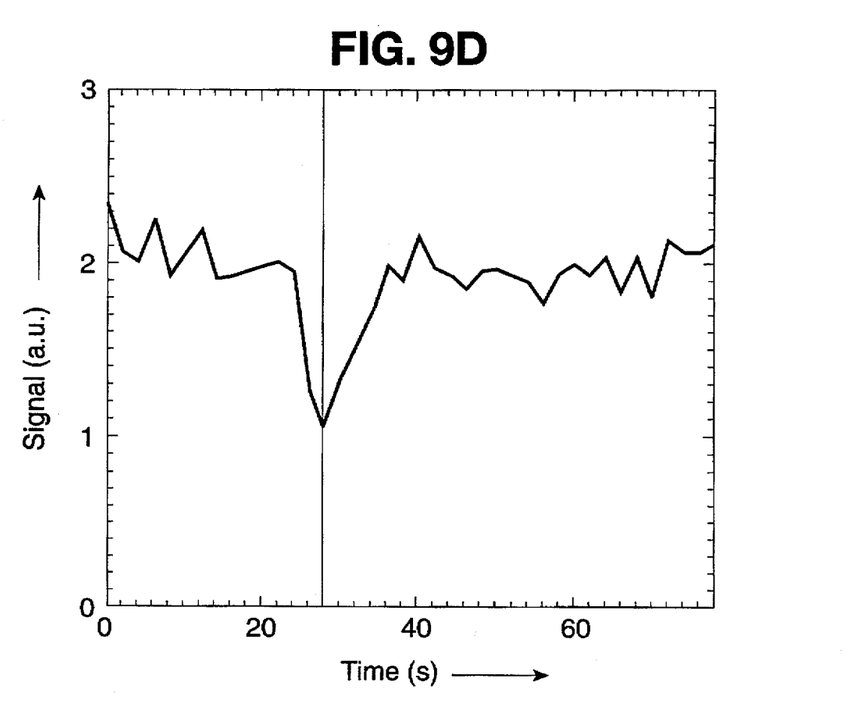
FIG. 9D show the bolus arrival time data in sub-acute stroke from a pixel contralateral to the infarct.

The results of the measurements of sub-acute brain infarction are shown in FIGS. 8A-8D and in FIGS. 9A-9D. Five slices (every third slice from a 3D dataset) are displayed going from infero-anterior to supero-posterior through the brain. Slice numbers are indicated at the top of the figure. Each of the rows shows: T2-weight data (FIG. 8A), calculated baseline intensity (FIG. 8B), rCBV (FIG. 8C), and arrival time (FIG. 8D). The signal baseline level, rCBV, and arrival time maps were calculated from the FS-BURST data (i.e., FIGS. 8B, 8C, and 8D). The location of the infarct is indicated with the white arrow in FIG. 8A, whereas part of the region from which time course data were examined is indicated with the black arrow in FIG. 8D. T2-weighted MRI (TE/TR=80/3000 ms) showed hyperintense regions in the infarcted hemisphere (FIG. 8A). The spread in arrival time in (FIG. 8D) is 7-8 s. The base line images (FIG. 8B) show hyperintensities similar to those observed in the T2-weighted data. Some signal loss is observed in the rCBV maps (FIG. 8C) at the site of the stroke, whereas some peripheral areas (especially in slices 34 and 37) showed increased rCBV. The most striking changes were seen in the arrival time maps. Regions surrounding the hyperintense areas in the T2-weighted maps appear dark, indicating late arrival of the bolus. The latter finding is consistent with the presence of "luxury perfusion" in the infarct penumbra.

Signal time course data from a pixel within the infarcted area (indicated with white arrow in T2-image of slice 34 in FIG. 8A), from two pixels adjacent to the infarct (black arrow in FIG. 8D) and from a contralateral normal appearing area are shown in FIGS. 9A-9D. In each graph, the arrival time of the bolus in the contralateral pixel is indicated with a vertical line. Although most pixels adjacent to the infarcted a region show an arrival time delay of 5-7 seconds, significant area remains with a normal or only a partially delayed bolus arrival time. Note the virtual absence of perfusion within the infarcted region (FIG. 9A), and the slightly (FIG. 9B) and the substantially (FIG. 9C) delayed bolus arrival adjacent to the infarct.

Thus, as illustrated through the preferred embodiment and the foregoing example, and as understood by further practicing the present invention, many advantages and attendant advantages are provided by the present invention, which provides a new modality for MRI detection of blood flow variations and abnormalities. Rapid 3D assessment of large regions may be performed. After, such an assessment, a smaller field of view with increased resolution may be selected to image observed pathological regions. Moreover, it may be understood that prior art MRI techniques that depend directly on quantitative changes in signal intensity are generally more susceptible to signal-to-noise limitations and spurious effects due to collateral blood supply. Thus, the present invention may detect blood flow abnormalities that are not detectable by prior art methods. Also, in comparison to other techniques not based on MRI, many of these advantages are further highlighted. For instance, the present invention may readily be employed in instances where Doppler Ultrasound techniques may be ineffective, such as for detecting blood flow variations near bone structure (e.g., cranium) or in regions other than large arteries.

Although the above description provides many specificities, these enabling details should not be construed as limiting the scope of the invention, and it will be readily understood by those persons skilled in the art that the present invention is susceptible to many modifications, adaptations, and equivalent implementations without departing from this scope and without diminishing its attendant advantages. It is therefore intended that the present invention is not limited to the disclosed embodiments but should be defined in accordance with the claims which follow.

We claim:

1. A method of generating magnetic resonance imaging information for detecting regions of abnormal blood flow in a body, comprising the steps of:

injecting a bolus of a magnetic resonance imaging contrast agent into the cardiovascular system of the body;

subjecting the body to a magnetic resonance imaging pulse sequence for obtaining a series of temporally spaced magnetic resonance signals or images from localized regions of stationary tissue in at least a part of said body into which the contrast agent passes; and providing an arrival delay time from the signals or images for the localized regions by fitting an analytical curve to the temporally spaced magnetic resonance signals obtained for the localized regions.

2. The method according to claim 1, further comprising the step of generating an arrival time map for a plurality of said localized regions, said arrival time map having a plurality of pixels corresponding to a respective plurality of said localized regions, with a visual characteristic of each pixel assigned according to the arrival delay time for the respective localized region.

3. The method according to claim 2, wherein said visual characteristic is color.

4. The method according to claim 2, wherein said visual characteristic is intensity.

5. The method according to claim 2, wherein said visual characteristic is a gray scale value.

6. The method according to claim 1, wherein said analytical curve includes terms that describe a gaussian time course of signal loss during the bolus passage, and a persistent signal loss after bolus passage.

7. The method according to claim 1, wherein said imaging pulse sequence is a frequency shifted BURST imaging pulse sequence.

8. The method according to claim 1, wherein said imaging pulse sequence images a two dimensional slice including a plurality of said localized regions, said localized regions thereby referred to as pixels.

9. The method according to claim 1, wherein said imaging pulse sequence images a three dimensional volume including a plurality of said localized regions, said localized regions thereby referred to as voxels.

10. The method according to claim 1, wherein said analytical curve is independent of a gamma-variate function.

11. The method according to claim 1, wherein said analytical curve is based on a quasi-constant pre-bolus signal level, a quasiconstant post-bolus signal loss related to bolus intensity, and a variable bolus arrival time.

12. A magnetic resonance imaging system for detecting regions of abnormal blood flow in a body, the cardiovascular system of which is injected with a bolus of magnetic resonance imaging contrast agent, said system comprising:

means for subjecting said body to a magnetic resonance imaging pulse sequence which induces a series of temporally spaced magnetic resonance signals in localized regions of stationary tissue in at least a part of said body into which the contrast agent passes;

means for obtaining said series of temporally spaced magnetic resonance signals;

means for providing an arrival delay time from the series of temporally spaced magnetic resonance signals for the localized regions by fitting an analytical curve to the temporally spaced magnetic resonance signals obtained for the localized regions.

13. The system according to claim 12, wherein said analytical curve includes terms that describe a gaussian time course of signal loss during the bolus passage, and a persistent signal loss after bolus passage.

14. The system according to claim 12, wherein said analytical curve is independent of a gamma-variate function.

15. The system according to claim 12, wherein said analytical curve is based on a quasi-constant pre-bolus signal level, a quasiconstant post-bolus signal loss related to bolus intensity, and a variable bolus arrival time.

16. The system according to claim 12, wherein said imaging pulse sequence is a frequency shifted BURST imaging pulse sequence.

* * * * *